United States Patent
Lalvani et al.

(10) Patent No.: US 12,201,642 B2
(45) Date of Patent: Jan. 21, 2025

(54) COMPOSITION FOR THE TREATMENT OF COVID-19

(71) Applicants: Kartar Singh Lalvani, London (GB); Robert Taylor, London (GB); Rohit Shelatkar, London (GB)

(72) Inventors: Kartar Singh Lalvani, London (GB); Robert Taylor, London (GB); Rohit Shelatkar, London (GB)

( * ) Notice: Subject to any disclaimer, the term of this patent is extended or adjusted under 35 U.S.C. 154(b) by 229 days.

(21) Appl. No.: 17/157,107

(22) Filed: Jan. 25, 2021

(65) Prior Publication Data
US 2022/0105110 A1    Apr. 7, 2022

(30) Foreign Application Priority Data
Oct. 1, 2020    (EP) .................................... 20000351

(51) Int. Cl.
| | | |
|---|---|---|
| *A61K 31/616* | (2006.01) | |
| *A61K 31/137* | (2006.01) | |
| *A61K 31/375* | (2006.01) | |
| *A61K 31/455* | (2006.01) | |
| *A61K 31/5415* | (2006.01) | |
| *A61K 31/593* | (2006.01) | |
| *A61K 31/7034* | (2006.01) | |
| *A61K 33/04* | (2006.01) | |
| *A61K 33/18* | (2006.01) | |
| *A61K 33/30* | (2006.01) | |
| *A61K 36/76* | (2006.01) | |
| *A61P 31/14* | (2006.01) | |

(52) U.S. Cl.
CPC .......... *A61K 31/616* (2013.01); *A61K 31/137* (2013.01); *A61K 31/375* (2013.01); *A61K 31/455* (2013.01); *A61K 31/5415* (2013.01); *A61K 31/593* (2013.01); *A61K 31/7034* (2013.01); *A61K 33/04* (2013.01); *A61K 33/18* (2013.01); *A61K 33/30* (2013.01); *A61K 36/76* (2013.01)

(58) Field of Classification Search
None
See application file for complete search history.

(56) References Cited

FOREIGN PATENT DOCUMENTS

| RU | 2237475 C1 | * 10/2004 | |
| WO | WO-8701285 A | * 3/1987 | ............. A61K 31/19 |

OTHER PUBLICATIONS

"COVID-19 related drugs." McKinsey & Company (Mar. 28, 2020): 1-3. (Year: 2020).*
Shi, Yufang, et al. "COVID-19 infection: the perspectives on immune responses." Cell Death & Differentiation 27.5 (Mar. 23, 2020): 1451-1454. (Year: 2020).*
Akhtar, Saeed, et al. "Nutritional perspectives for the prevention and mitigation of COVID-19." Nutrition reviews 79.3 (Jul. 15, 2020): 289-300. (Year: 2020).*
Chaari, Ali, et al. "Importance of dietary changes during the coronavirus pandemic: how to upgrade your immune response." Frontiers in Public Health 8 (Aug. 27, 2020): 1-24. (Year: 2020).*

* cited by examiner

*Primary Examiner* — Bethany P Barham
*Assistant Examiner* — Peter Anthopolos
(74) *Attorney, Agent, or Firm* — Laubscher & Fretwell, P.C.

(57) ABSTRACT

A formulation provides a unique synergistic composition for the treatment of the novel Coronavirus (COVID-19). Due to multiple mechanisms and synergy of action of the ingredients involved, using drug and nutrient therapy to support the body's natural immune response, it can provide a significant advantage to currently used therapies and may also be administered prophylactically. In its optimal embodiment the composition can be prepared in solid (tablet or capsule) or liquid form, containing Aspirin or any natural salicinoid, Phenylephrine, Promethazine, Vitamin D, Vitamin C, Niacinamide, Iodine Zinc and Selenium.

10 Claims, No Drawings

COMPOSITION FOR THE TREATMENT OF COVID-19

This application claims priority of Application No. EP20000351 filed Oct. 1, 2020 entitled Novel Composition for the Treatment of COVID-19. The entire content of this application is incorporated herein by reference.

TECHNICAL FIELD

This invention concerns the development of a synergistic composition in a solid or liquid formulation for the treatment of the novel Coronavirus disease (COVID-19). The proposed formula includes both drug and nutrient ingredients to induce rapid treatment of typical COVID-19 symptoms, including fever, dry cough and respiratory distress, as well as naturally boosting the innate and adaptive immune system.

BACKGROUND ART

Coronavirus comprises of a large family of viruses that are common in humans as well animals, including camels, cattle, cats, and bats. There are several different strains of coronavirus, with SARS-CoV-2 being the novel coronavirus that causes coronavirus disease 2019 (COVID-19). Towards December 2019, this novel Coronavirus was identified as a cause of upper and lower respiratory tract infections in Wuhan, a city in the Hubei Province of China. It rapidly spread, resulting in an epidemic throughout China, before spreading to other parts of the world before the WHO declared a global pandemic.

Transmission of COVID-19 is mainly reported via droplet transmission. The other possible modes of transmission involve touching surfaces contaminated by the virus and then touching the mouth, nose, or possibly the eyes.

Clinical features:
 a. Incubation period: It is not exactly known but presumed to be between 2 to 14 days after exposure to the virus.
 b. Spectrum of illness severity:
   Most infections are asymptomatic or self-limiting, though the disease can be serious, which is often fatal. COVID-19 tends to cause more severe illness in the elderly population or in patients with comorbidities (such as heart disease, asthma or diabetes). Severe illness includes hypoxemia, respiratory failure, and multi-organ dysfunction syndrome.
 c. Age affected: mostly middle aged (>50 years) and elderly populations. Symptomatic infection in children and infants is uncommon.

Clinical Presentation: Common clinical features at the onset of illness are fever, fatigue, dry cough, myalgias and dyspnea. Pneumonia appears to be the most common symptom and severely affects the population. Acute respiratory distress syndrome is another common feature among the infected. Other symptoms include headache, sore throat, rhinorrhea and gastrointestinal symptoms.

About 80% of confirmed COVID-19 cases suffer from only mild to moderate disease and nearly 13% have severe disease (dyspnea, respiratory frequency ≥30/minute, blood oxygen saturation≤93%). Critical illness (respiratory failure, septic shock, and/or multiple organ dysfunction/failure) is noted in only less than 6% of cases.

Preventive measures:
 Use of personal protective equipment including masks, hand hygiene practices, social distancing and isolation, case detection and contact tracing have been used as ways to reduce transmission. To date, no specific antiviral treatment or vaccine has proven effective; hence, infected patients primarily rely on the limited available symptomatic treatment and supportive care.

COVID-19 infected patients are categorized as follows:
 1. Asymptomatic but positive
 2. Symptomatic, URTI without co-morbidity
 3. Symptomatic, URTI with co-morbidity
 4. Pneumonia (LRTI) without respiratory failure
 5. Pneumonia (LRTI) with respiratory failure
 6. Pneumonia (LRTI) with respiratory failure multi organ dysfunction syndrome The current therapies used in COVID-19

Current treatment includes a combination of drugs including antiviral, antimalarial (Hydroxychloroquine) and antibiotics (Azithromycin). The dose and combination of these medications depends on the severity and class of patient infected. An observational study found no clinical benefit associated with hydroxychloroquine leading the WHO to suspend all hydroxychloroquine studies.
 a. Antiviral therapy—No anti-viral therapy has been proven to work for COVID-19 in humans. Multiple RCTs are ongoing (Remdesivir, Lopinavir, Ritonavir, Ribavirin, Oseltamivir).
 b. ACE inhibitors—(ACEi)/angiotensin receptor blockers (ARBs) are under trial since the SARS-CoV-2 virus binds to the ACE2 receptor for cellular entry.
 c. Interferons—SARS CoV2 attenuates the interferon (IFN) response of the innate immune system but has not yet shown in vitro beneficial effects.
 d. Antimalarial (chloroquine/hydroxychloroquine)—hampers the low pH dependant steps of viral replication. Proposed to be used for prophylaxis, however, lacks evidence.
 e. Use of ILK-1 and IL-6 inhibitors to reduce cytokine storm in COVID-19.
 f. Antibacterial agents initiated to treat secondary bacterial pneumonia.
 g. Research focusing on therapies involving plasma collected from recovered patients.

There is therefore an acute need for effective symptomatic therapy combined with a natural boost to the immune system.

DISCLOSURE OF INVENTION

The object of the present invention is to develop a synergistic novel composition for the treatment of COVID-19 to induce rapid treatment across an array of typical COVID-19 symptoms and to naturally assist the body fight the specific SARS-CoV-2 infection.

The following form the key components of the invention, but are not to be construed as limiting the invention in scope or spirit, as possible modifications will be apparent from the disclosure to those skilled in this art.

Aspirin—This is not generally used or recommended for the treatment of COVID-19, despite its anti-viral, anticoagulant and anti-inflammatory effects. Aspirin has an inhibitory effect on platelet aggregation and has been shown to alter the profile of proteins in platelets involved in directing innate immune response to the site of injury and could thereby reduce lung injury.

Aspirin has a well-known capacity to inhibit NF-kB. It efficiently blocks influenza virus replication in vitro and in vivo in a mechanism involving impaired expression of proapoptotic factors, subsequent inhibition of caspase activation, as well as blockage of caspase-mediated nuclear export of viral ribonucleoproteins. It showed no toxic side-effects or the tendency to induce resistant virus variants, hence may be suitable as an anti-influenza agent. (Cellular Microbiology (2007) 9(7), 1683-1694.)

Aspirin was found to be highly effective against influenza A H1N1 virus. The antiviral activity against further respiratory RNA viruses was less distinct. (Influenza Other Respir Viruses. 2017 January; 11(1): 85-92.)

Studies have shown that the nonspecific COX-2 inhibitor, aspirin, can reduce the yield of HCMV in cultures of smooth muscle cells by a factor of 2-3. Experimental studies have shown that the COX-2 inhibitors are acting by blocking the production of $PGE_2$. (PNAS March. 19, 2002 99 (6) 3932-3937.)

Acetylsalicylic acid and indomethacin dose-dependently exert stimulatory effects on the production of pro-inflammatory cytokines in whole blood. Aspirin shows dose-dependent immunomodulating effects on pro-inflammatory cytokine production. (Scandinavian Journal of Immunology, 60(4), 412-420.)

Aspirin has immunoregulatory potential in relevance to immune tolerance. It also displays some intriguing traits to modulate the innate and adaptive immune responses. (International immunopharmacology 12(1):10-20.)

Aspirin is well known to function as a blood thinning agent through inhibition of the enzyme Cox-1, which produces thromboxane A-2, necessary for platelet aggregation. Images of lung function in Covid-19 patients have found a lack of blood flow indicative of clotting within the small blood vessels in the lung. The Coronvirus spike protein binds to the ACE2 receptor and this binding complex may form a site for thrombosis. This specific intravascular clotting mechanism may account for the common clinical feature observed in Covid-19 patients of hypoxia, or very low oxygen, despite a lack of any vital warning signs of breathlessness.

Aspirin inhibits COX-2 mediated production of prostaglandins but switches on COX-2's ability to produce novel protective lipid mediators. COX-2 inhibitors can abrogate the virus-mediated induction of prostaglandin E2 accumulation. (Proceedings of the National Academy of Sciences, 99(6), 3932-3937.)

Phenylephrine—This is a selective $\alpha_1$-adrenergic receptor agonist. It is a nasal decongestant which has been found to reduce nasal airway resistance. (CMAJ. 2014 Feb. 18; 186(3): 190-199.)

It has pulmonary and systemic vasoconstrictor effects and is commonly used in intensive care. (Anesthesiology 7 1997, Vol.87, 18-25.)

Promethazine—is a derivative of phenothiazine and an antihistaminic used in treating symptoms of asthma, pneumonia, or other lower respiratory tract infections. (Biomed Res Int. 2013; 2013: 151509.) Anti-histamines block airway inflammation and bronchoconstriction caused by histamine release from mast cells. Mast cell activation and Histamine release may contribute to the inflammation associated with COVID-19 infection. Patients with COVID-19 have systemic elevation of pro-inflammatory cytokines IL-6 and TNF-α. The overactivation of mast cells and release of cytokines might also have a role in the development of pulmonary fibrosis in COVID-19 patients. Promethazine may also act in COVID-19 patients as a cough suppressant, acting on part of the brain to reduce the need to cough.

Niacinamide—Vitamin B3 can be administered in two main supplemental forms; Nicotinamide (also known as Niacinamide) or niacin (or nicotinic acid). Both forms are required to maintain healthy cells but at high doses, nicotinamide and niacin can have different effects. An immunomodulatory role for nicotinamide in a wide variety of experimental systems has been reported, including modulation of cytokine action. As Nicotinamide is recognised for its lung protective properties it has been recommended in COVID patients as soon as coughing begins (Shi, Y., Wang, Y., Shao, C. et al. COVID-19 infection: the perspectives on immune responses. Cell Death Differ 27, 1451-1454 (2020)). Nicotinamide is emerging as a therapeutic agent with activity against both M. tuberculosis and HIV. (Clinical infectious Diseases, Volume 36. Issue 4, 15 February 2003. Pages 453-460.) Niacin may play a role in T-cell immune activation as it may control the excess tryptophan oxidation, correcting tryptophan depletion, and improve CD4 recovery. The Pharmacokinetics of nicotinamide and its effect on blood pressure, pulse and body temperature in normal human volunteers has been studied. (Radiotherapy and Oncology, Volume 25, Issue 1, September 1992, Pages 37-42.)

Vitamin D—The role of vitamin D in immunomodulation has a significant impact on immune function. A causal relationship exists between vitamin D function and innate and adaptive immunity to infections. The mechanisms underlying vitamin D immune actions could be attributed to a paracrine feedback loop that reduces inflammation as well as influencing the differentiation fate of activated CD4 T cells, or the enhancement of suppressor T-cell function; (Current Opinion in Otolaryngology & Head and Neck Surgery, 19(3), 224-228). Vitamin D receptor (VDR) is expressed by the majority of the immune cells, including B and T lymphocytes, monocytes, macrophages, and dendritic cells. Vitamin D and VDR signalling together have a suppressive role on autoimmunity and an anti-inflammatory effect, promoting dendritic cell and regulatory T-cell differentiation and reducing T helper Th 17 cell response and inflammatory cytokines secretion. (Nutrients. 2018 November; 10(11): 1656.) Vitamin D is a potent immune modifying micronutrient and if vitamin D status is sufficient, it could benefit vulnerable adults, in particular those 70+ years and older who are 'cocooning' during the COVID-19 outbreak. (TILDA study, April 2020.) Evidence suggests COVID-19 patients with high vitamin D levels are more likely to survive the disease. Correlation has been found between countries reporting low vitamin D levels with highest mortality and COVID-19 infection rates. Vitamin D may reduce COVID-19 severity by suppressing 'cytokine storm' in patients. This serious overreaction of the body's immune system occurs when excessive or uncontrolled levels of cytokines are released, which then activate more immune cells, resulting in hyperinflammation, severe lung damage, acute respiratory distress syndrome (ARDS). Vitamin D therefore helps boost the innate immune response in COVID-19 but also suppress overreaction when necessary.

Vitamin C—Because Vitamin C contributes to immune defence by supporting various cellular functions of both the innate and adaptive immune system. Vitamin C promotes the oxidant scavenging activity potentially protecting against environmental oxidative stress. Vitamin C accumulates in phagocytic cells, such as neutrophils, and can enhance chemotaxis, phagocytosis, generation of reactive oxygen species, and ultimately microbial killing. It is also needed for apoptosis and clearance of the spent neutrophils from sites of infection by macrophages, thereby decreasing necrosis/NETosis and potential tissue damage. Supplementation with vitamin C appears to be able to both prevent and treat respiratory and systemic infections. (Nutrients. 2017 Nov 3; 9(11). pii: E1 211.) Vitamin C shows in vivo anti-viral immune responses at the early time of infection, especially against influenza virus, through increased production of IFN-α/β. (Immune Netw. 2013 April; 13(2): 70-74.)

Zinc—a trace mineral that is found in cells throughout the body. Various immune cells show decreased function after zinc depletion. In monocytes, all functions are impaired, whereas in natural killer cells, cytotoxicity is decreased, and in neutrophil granulocytes, phagocytosis is reduced. The normal functions of T cells are impaired with zinc depletion, but autoreactivity and alloreactivity are increased. B cells undergo apoptosis. Impaired immune functions due to zinc deficiency are shown to be reversed by an adequate zinc supplementation. (The Journal of Nutrition, Volume 133, Issue 5, May 2003, Pages 1452S-1456S.)

Zinc supplementation reduced the number of days of acute lower respiratory infection in Thai children. (Pediatr Rep. 2019 May 23; 11(2): 7954.)

Iodine—is an essential mineral required in trace amounts to make thyroid hormones which control metabolism. It is required for the function of all organ systems. Thyroid hormones directly affect multiple branches of the immune system. Studies have indicated complex networks operating between human immune cells and thyroid-related molecules, through which iodine may play a fundamental role in regulating the function of immune cells.

Selenium—an antioxidant and its status may affect the function of cells of both adaptive and innate immunity. Supranutritional selenium promotes proliferation and favours differentiation of naive CD4-positive T lymphocytes toward T helper 1 cells, thus supporting the acute cellular immune response. Its supplementation is beneficial in diseases, most notably with respect to HIV and influenza A virus (IAV) infections. (Adv Nutr. 2015 January; 6(1): 73-82.)

The object of the present invention is to develop a composition for the management of Coronavirus disease (COVID-19) that overcomes the disadvantages of conventional treatment, especially in a non-hospital setting.

It has been widely recommended that paracetamol is routinely used in COVID-19, despite the side effects associated with paracetamol. However, in an unpublished clinical case study of COVID-19 (Data on file, London, April 2020) (severe symptoms but not hospitalised), including on average 9-12-days of persistent elevated temperature remaining consistently above 39 degrees centigrade, treatment with paracetamol alone was switched to the present inventive combination of Aspirin 300 mg per day, Promethazine 15 mg per day, Niacinamide 160 mg (ten times the European NRV value), each in line with the invention. Clinical observations were made following this change in treatment administration.

A measured improvement in symptoms was observed within 12 hours of the intervention, including a case of reduction in body temperature to normal levels within 6 hours.

This rapid reduction in symptoms is not found and has never been reported with Aspirin alone, or with Niacinamide alone, or Promethazine alone, nor is this combination obvious.

It is believed that this is the first reported case study of such a finding using a combination of specific doses of Aspirin, Promethazine and Niacinamide.

The product which is the subject of the invention provides a better alternative to conventional treatment by specific focus on:

Rapid immediate treatment of fever or hyperpyrexia without side effects.

Treatment of dry cough associated with COVID-19.

Blockage of influenza virus replication through the mechanism of COX-2 inhibition.

Naturally boosting both the innate and adaptive immune system.

Targeting the novel respiratory aspects of the disease and endothelial vascular thrombosis, which differentiates COVID-19 from influenza conditions and pneumonia.

Preventing the hypoxia without breathlessness that is commonly associated with COVID-19 by reducing thrombosis within blood vessels in the lung.

Modulation of cytokine action through multiple mechanisms.

Reduce inflammatory cytokine storm and vascular thrombosis in sites across the body other than the lung, thereby reducing the risk of heart attack, stroke and other complications associated with COVID-19.

Disclosure of the ideal version of the invention is as follows:

Aspirin—300 mg
Phenylephrine—20 mg
Promethazine—15 mg
Vitamin D—4,000 IU
Vitamin C—1.5 g
Niacinamide—160 mg
Iodine—200 mcg
Zinc—30 mg (elemental)
Selenium—165 mcg (elemental)

In an acceptable size of solid dose form, this gives the following formulation for a three times daily capsule or tablet:

Aspirin—100 mg
Phenylephrine—6.67 mg
Promethazine—5 mg
Vitamin D—1,333.33 IU
Vitamin C—0.5 g
Niacinamide—53.33
Iodine—66.67 mcg
Zinc—10 mg (elemental)
Selenium—55 mcg (elemental)

A total of three tablets or capsules may be taken every day by the patient for 1-6 weeks until a beneficial improvement, partial or complete recovery is achieved.

The following examples are some of the possible alternative forms of the invention. These examples are not to be construed as limiting the invention in scope or spirit, as possible modifications to the invention will be apparent from the disclosure to those skilled in this art.

EXAMPLE 1

Aspirin—500 mg
Phenylephrine—20 mg
Promethazine—25 mg
Vitamin—10,000 IU
Vitamin C—4 g
Niacinamide—500 mg
Iodine—250 mcg
Zinc—75 mg (elemental)
Selenium—200 mcg (elemental)

EXAMPLE 2

Aspirin—500 mg
Phenylephrine—10 mg
Promethazine—25 mg
Vitamin D—4000 IU

Vitamin C—2 g
Niacinamide—160 mg
Iodine—250 mcg
Zinc—40 mg (elemental)
Selenium—100 mg (elemental)

EXAMPLE 3

Aspirin—500 mg
Phenylephrine—20 mg
Promethazine—20 mg
Vitamin D—4000 IU
Vitamin C—2 g
Niacinamide—160 mg
Iodine—200 mcg
Zinc—40 mg (elemental)
Selenium—100 mg (elemental)

EXAMPLE 4

Aspirin—500 mg
Phenylephrine—20 mg
Promethazine—20 mg
Vitamin D—4000 IU
Vitamin C—2 g
Niacinamide—160 mg
Iodine—200 mcg
Zinc—40 mg (elemental)
Selenium—100 mg (elemental)

EXAMPLE 5

Aspirin—325 mg
Phenylephrine—20 mg
Promethazine—15 mg
Vitamin D—10,000 IU
Vitamin C—4 g
Niacinamide—160 mg
Iodine—200 mcg
Zinc—75 mg (elemental)
Selenium—200 mcg (elemental)

EXAMPLE 6

Aspirin—300 mg
Phenylephrine—20 mg
Promethazine—15 mg
Vitamin D—3000 IU
Vitamin C—2 g
Niacinamide—64 mg
Iodine—150 mcg
Zinc—37 mg (elemental)
Selenium—100 mg (elemental)

EXAMPLE 7

Aspirin—300 mg
Phenylephrine—10 mg
Promethazine—12 mg
Vitamin D—3000 IU
Vitamin C—4 g
Niacinamide—64 mg
Iodine—150 mcg
Zinc—75 mg (elemental)
Selenium—200 mcg (elemental)

EXAMPLE 8

Aspirin—100 mg
Phenylephrine—10 mg
Promethazine—10 mg
Vitamin D—1000 IU
Vitamin C—0.5 g
Niacinamide—18 mg
Iodine—150 mcg
Zinc—10 mg (elemental)
Selenium—50 mcg (elemental)

The natural glucoside of o-hydroxybenzylalcohol, Salicin, obtained from bark of the willow (Salix) may be used as a replacement for Aspirin in the product, as the mechanism of action is similar to aspirin through COX-2 inhibition. Studies have shown that drugs that block enzyme COX-2, thereby reduce the manufacture of Prostaglandin E that helps viruses multiply and can have anti-viral effects.

MEANS OF ADMINISTRATION

The invention can be prepared most conveniently in solid tablet or capsule form, or can be prepared in liquid form depending on suitability, solubility and stability of ingredients present. Other factors like pharmacokinetics and bioavailability can affect the route of administration.

The invention claimed is:

1. A pharmaceutical composition for the specific treatment or prophylactic use against COVID-19 in any form, via any biological route, consisting essentially of acetylsalicylic acid, promethazine, a B3 Vitamin, and optionally one or more carriers or excipients.

2. A composition according to claim 1, wherein the B3 Vitamin is selected from the group consisting of niacinamide, niacin, and nicotinic acid.

3. A composition according to claim 1, wherein the composition is prepared for administration as a single or multiple dose, either in solid or liquid dosage form.

4. A pharmaceutical composition beneficial as complementary therapy to be indicated in COVID-19 in any form, via any biological route, consisting essentially of, acetylsalicylic acid, phenylephrine, promethazine, and optionally at least one of a B3 vitamin and one or more carriers or excipients, the amount of acetylsalicylic acid being not lower than 20 mg and not greater than 600 mg.

5. A pharmaceutical composition according to claim 4, wherein the amount of promethazine is in the range of 3 mg to 8 mg or 12 mg to 75 mg.

6. A pharmaceutical composition according to claim 4, wherein the amount of acetylsalicylic acid is greater than 100 mg and less than 600 mg.

7. A composition according to claim 4, wherein the composition is prepared for administration as a single or multiple dose either in solid or liquid dosage form.

8. A pharmaceutical composition for the specific treatment or prophylactic use against COVID-19 in any form, via any biological route, consisting essentially of acetylsalicylic acid in an amount greater than 100 mg and less than 600 mg, promethazine, a B3 vitamin, and optionally at least one of:
    (a) phenylephrine;
    (b) an average dietary level intake of vitamin D and iodine;
    (c) an average dietary level intake of vitamin C, zinc and selenium; and
    (d) one or more carriers or excipients.

9. A pharmaceutical composition according to claim 8, wherein the amount of vitamin D is not lower than 100IU and not exceeding 30,000IU and the amount of iodine is not lower than 10mcg and not exceeding 500mcg.

10. A pharmaceutical composition according to claim 8, wherein the amount of vitamin C is not lower than 10 mg and not exceeding 7g, the amount of Zinc is not lower than 3 mg and not exceeding 250 mg and the amount of Selenium is not lower than 5mcg and not exceeding 500mcg.

* * * * *